United States Patent [19]

Valchanov et al.

[11] Patent Number: 4,979,501
[45] Date of Patent: Dec. 25, 1990

[54] METHOD AND APPARATUS FOR MEDICAL TREATMENT OF THE PATHOLOGICAL STATE OF BONES

[75] Inventors: Vyacheslav D. Valchanov; Peter M. Mihaylov; Todor K. Patrashkov; Stoyan S. Manolov; Todor P. Kerin, all of Sofia, Bulgaria

[73] Assignee: Vissh Voennomedicinski Institut, Sofia, Bulgaria

[21] Appl. No.: 318,593

[22] PCT Filed: May 18, 1988

[86] PCT No.: PCT/BG88/00001

§ 371 Date: Feb. 13, 1989

§ 102(e) Date: Feb. 13, 1989

[87] PCT Pub. No.: WO88/09190

PCT Pub. Date: Dec. 1, 1988

[30] Foreign Application Priority Data

May 19, 1987 [BG] Bulgaria ............................ 79804

[51] Int. Cl.$^5$ ............................................. A61N 1/00
[52] U.S. Cl. .................................. 128/24 A; 128/419 F
[58] Field of Search .................... 128/328, 29 A, 804, 128/419 F

[56] References Cited

U.S. PATENT DOCUMENTS 4,530,360  7/1985  Duarte ........................... 128/419 F
4,610,249  9/1986  Makofski et al. .................. 128/328
4,796,613  1/1989  Hermann et al. ........... 128/328 S X

FOREIGN PATENT DOCUMENTS 3122056  12/1982  Fed. Rep. of Germany .
2084439   4/1982  United Kingdom .

OTHER PUBLICATIONS

Sauerbruch, T. et al., "Fragmentation of Gallstones", NEJM vol. 314, No. 13, Mar. 27, 1986, pp. 818–822.
Bassett, C. A. "Electrical Effects in Bone", pp. 18–24 only, (date unknown).
Chaussey, C. et al. "Shock Wave Treatment for Stones in the Upper Urinary Tract", Sympon Surgery, Urolgic Clinics of N. America, vol. 10, No. 4, Nov. 1983.
Diffenback-Beck, Koptchev, Trawmatologya no Oporno-Dvigatelnya Aparat, Sofia, Medizina i, Fizkoultoura, 1976, p. 137 (Together with English excerpt).
Fragmentation of Gallstones by Extracorporeal Shock Waves, Sauerbruch, Tilman, MD et al., *The New England Journal of Medicine*, vol. 314, No. 13, pp. 818–822 (1986).
Medizin in Unserer Zeit, vol. 4, No. 1, 1980, Verlag Chemie, GMBH, (Weinheim, West Germany), B. Forssmann et al.: "Stosswellen in der Medizin", pp. 10–14.
Work in Progres #1, The Lithotriptor and its Potential Use in the Revision of Total Hip Arthroplasty, Arthroplasty, Orthopaedic Review, vol. XVI, No. 1, pp. 81–85 (Jan. 1987).
Munchener Medizinische Wochenschrift, Stosswellentherapie zur Behandlung von Nierensteinen, Chaussey, CH et al., vol. 125, No. 8, pp. 151–155 (1988).
Extracorporeally Induced Destruction of Kidney Stones by Shock Waves, Chaussy, Ch. et al., The Lancet, pp. 1265–1267 (1980).
Effect of High Energy Shock Waves on Bony Tissue, Graff, J. et al., p. 260, Cairo, Nov. 1987.
Effects of Shock Waves on the Structure and Growth of the Immature Rat Epiphysis, Yeaman, Leslie D., et al., The Journal of Urology, vol. 141, pp. 670–673 (1989).
Tabor's Cyclopedic Medial Dictional (1989) pp. 233,269.
Extracorporeal Shock-Wave Lithotripsy: A Review Bashkoff, Eric et al., The Mount Sinai Journal of Medicine, vol. 55, No. 4, pp. 288–291 (1988).

*Primary Examiner*—Francis Jaworski
*Attorney, Agent, or Firm*—Herbert Dubno

[57] ABSTRACT

A method is disclosed for medically treating a patient suffering from a pathological bone condition of a limb, which comprises the steps of: anesthetizing the patient; fixing the limb affected with the pathological bone condition and centering its pathological site; treating the pathological site, once, consecutively, and extracorporeally with impact waves of from 300 to 600 impacts with a frequency of impacts of from 0.5 to 4 per second at a pressure of from 700 to 2500 bars and a pulse duration of from 0.5 to 4 microseconds for a period of 10 to 120 minutes; and subsequently immobilizing the limb for a period of from 15 to 90 days.

9 Claims, 7 Drawing Sheets

METHOD AND APPARATUS FOR MEDICAL TREATMENT OF THE PATHOLOGICAL STATE OF BONES

FIELD OF THE INVENTION

This invention relates to a method and an apparatus for medical treatment of bone pathology which finds application in orthopaedic traumatologic practice for medical treatment of pseudoarthrosis, delayed consolidation, bone deformations, correction of the length of long tubular bones, performing arthrodesis, acceleration of the normal bone knit, treatment of bone tumors, aseptic necrosis, delay of bone growth (epiphysiodesis), a.o.

BACKGROUND OF THE INVENTION

In a known method for medical treatment of pseudoarthrosis, delayed consolidation and bone deformations, after anesthesis the skin of the limb in the place of injury is cleaned to prepare for operation and then the bone is drilled through the skin in several places and the limb is immobilized. See Diffenbach-Beck I. Koptchev, Trawmatologya na oporno-dvigatelnaya aparat; Sofia, Medizina i Fizkoultoura; P. 137 (1976).

The drawbacks of this method lie in that it is invasive and frequently there occur complications, such as suppurations, osteomyelitis. There are not provided proper conditions for consolidation and, therefore, the method is not sufficiently effective.

Another known operative method for medical treatment consists in that, after anesthesis of the limb, the latter is fixed to the operation table, there is performed by operation a penetration to the bone, the periosteum is opened and the edges of the injured bone ends are scraped, while in case of bone deformations a bone triangle is cut out. A proper or preserved bone transplant is put in place. The fragments are aligned and are osteosynthesized with different materials. The periosteum and the soft tissues are restored and finally there is effected an external immobilization for a period of from 60 to 180 days. See R. Watson-Jones, *Fractures and Joint Injuries*, Vol. 1, pp 22–50 (1976).

The drawbacks of this method lie in that it is invasive with the possibility of post-operation complications occurring. A prolonged stay in the hospital is required. After the healing of the injury, a second operation is necessary for the removal of the osteo-sythesizing materials. In some cases there are several operative interventions necessary in the event of relapse.

A known apparatus for the fragmentation of kidney stones, the design of which is similar to that of the apparatus for medical treatment of bone pathology according to the present invention, comprises a generator of impact waves, over which there is disposed the patient carriage, underneath which there is fastened the head of an ultrasonic emitter, the vertical axis of which coincides with the vertical axis of the generator of impact waves and passes through the zone of fragmentation of the kidney stones. The generator of impact waves consists of a housing, shaped as a vessel containing an acoustic liquid, in the bottom end of which there is disposed a discharger which is covered by the liquid contained in the housing, and in its top end there is provided a flexible membrane see U.S. Pat. No. 4,610,249.

The drawback of this device is in that in cannot be used for medical treatment of bone pathology.

OBJECTS OF THE INVENTION

It is therefore a general object of this invention to develop a method for medical treatment of bone pathology which is non-operative, extracorporal, ambulatory, and can shorten the duration of the recovery process.

It is another object of this invention to develop an apparatus for the treatment of bone pathology which is of compact design and makes possible a quick and painless carrying out of the treatment.

SUMMARY OF THE INVENTION

The object is achieved by a method for medical treatment of bone pathology in which, after anesthesia, the limb is fixed to the carrying carriage of the apparatus and is finally immobilized. According to the invention, after the fixation of the limb and the centering of the pathological place and before the immobilization, it is subjected once, consecutively and extracorporally to the action of 300 to 6000 impact waves with a frequency of 0.5 to 4 per second, at a pressure in the range of from 700 to 2500 bars, at a pulse duration of from 0.5 to 4 microseconds for 10 to 120 minutes, with a subsequent immobilization from 15 to 90 days.

The object is also achieved by a method for medical treatment of bone pathology, pseudoarthrosis, delayed consolidation and bone deformations, in which the treatment at the site of pathology is effected by impact waves of from 1000 to 5000 impacts with a frequency of 1 to 2 per second, at a pressure of from 1200 to 2000 bars and pulse duration of from 1.5 to 3 microseconds for 20 to 110 minutes, with a subsequent immobilization of from 40 to 90 days.

The object is also achieved by another method for medical treatment of bone pathology for the correction of the length of long tubular bones, in which a device for extrafocal fixation is placed on the bone and the site of pathology is subjected to the action of impact waves of from 1000 to 6000 impacts with a frequency of 1 to 3 per second, at a pressure of from 1100 to 1700 bars and a pulse duration of from 1 to 3.5 microseconds for 30 to 115 minutes and subsequent immobilization of from 60 to 85 days.

The object is also achieved by a method for medical treatment of bone pathology for extracorporal performance of arthrodesis, in which the pathological place is subjected to the action of impact waves of from 750 to 6000 impacts with a frequency of from 0.5 to 3.5 per second, at a pressure of from 1200 to 2500 bars and pulse duration of from 0.5 to 2.5 microseconds over 15 to 120 minutes, and subsequent immobilization of from 30 to 80 days.

The object is also achieved by a method for medical treatment of bone pathology for acceleration of the normal bone knit, in which the site of pathology is subjected to the action of impact waves of from 300 to 3000 impacts, with a frequency of from 1 to 3.5 per second at a pressure of from 700 to 1500 bars and a pulse duration of from 1.5 to 4 microseconds for 10 to 90 minutes, and subsequent immobilization of from 15 to 60 days.

The object is also achieved by a method for medical treatment of bone pathology in the case of bone tumors, in the which the pathological place is subjected to the action of impact waves of from 500 to 5000 impacts with a frequency of from 0.5 to 4 per second, at a pressure of from 850 to 1700 bars and pulse duration of from 1.5 to 3.5 microseconds over 15 to 95 minutes, and subsequent immobilization of from 15 to 60 days.

The object is also achieved by a method for medical treatment of bone pathology in the case of delay of bone growth (epiphysiodesis), in which the pathological place is subjected to the action of impact waves of from 1000 to 5500 impacts with a frequency of from 1 to 4 per second at a pressure of from 950 to 1900 bars and a pulse duration of from 0.5 to 3.5 microseconds over 20 to 110 minutes, and subsequent immobilization of from 15 to 90 days.

The object is also achieved by a method of medical treatment of bone pathology in the case of aseptic necrosis, in which the pathological place is subjected to the action of impact waves of from 350 to 4000 impacts with a frequency of from 1 to 2.5 per second at a pressure of from 750 to 1600 bars and a pulse duration of from 1.5 to 3 microseconds over 10 to 105 minutes, and subsequent immobilization of from 15 to 30 days.

The object is also achieved by an apparatus which comprises a housing, inside which there is disposed a generator of impact waves, on the base of which there are fastened guiding rolls which are in contact with the internal surface of the outer housing, opposite to which there is disposed an x-ray generator. The top end of the generator of impact waves is shaped as a vessel containing a transmitting medium, which is an acoustic liquid, and it covers the discharger fastened to the bottom of the vessel, while in its top end there is disposed a flexible membrane. Over the generator of impact waves there is disposed a light diaphragm, and over it there is disposed an electronic optical converter, which is connected to a television camera, the longitudinal axis of which coincides with the longitudinal axis of the x-ray generator, and its point of intersection with the longitudinal axis of the light diaphragm forms the point of action. To the outer housing, behind the television camera, there is positioned a protective barrier.

The object is also achieved by an apparatus in which the generator of impact waves is rigidly connected to the central part of a carring arm, which can rotate around its axis and is connected to the external housing.

The advantages of the invention lie in that the medical treatment is non-operative, extra-corporal, ambulatory and less dangerous to the health of the patient. The potential for complications is reduced a minimum. The duration of treatment is reduced, too. The apparatus is compact, convenient and easy to operate and repair.

BRIEF DESCRIPTION OF THE DRAWINGS

For a better understanding of the invention reference should be made to the accompanying drawings in which there is illustrated and explained a preferred embodiment of the invention. In the drawings.

SPECIFIC DESCRIPTION OF THE DRAWINGS

Figure 1:
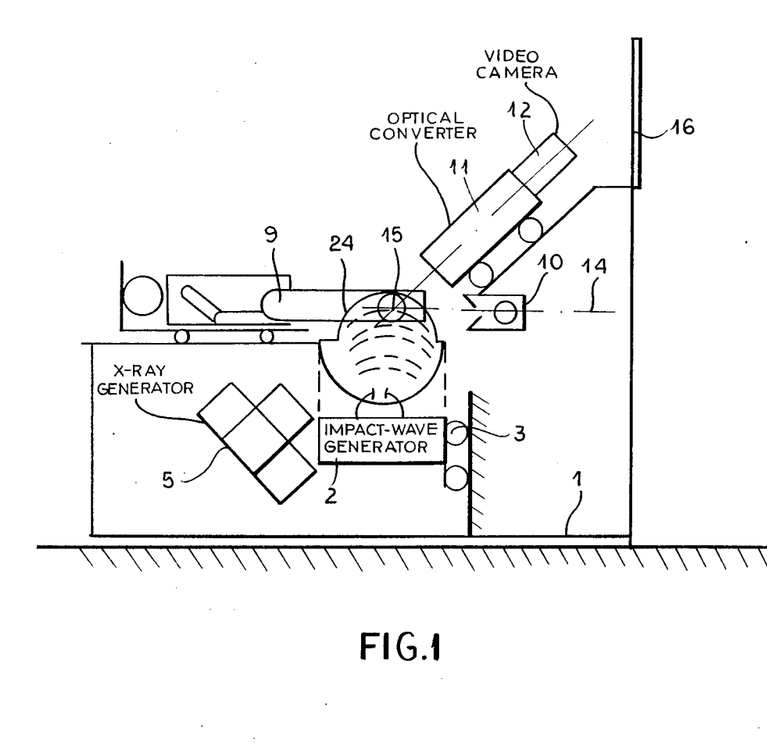
FIG. 1 is a general view of the apparatus.
Figure 2:
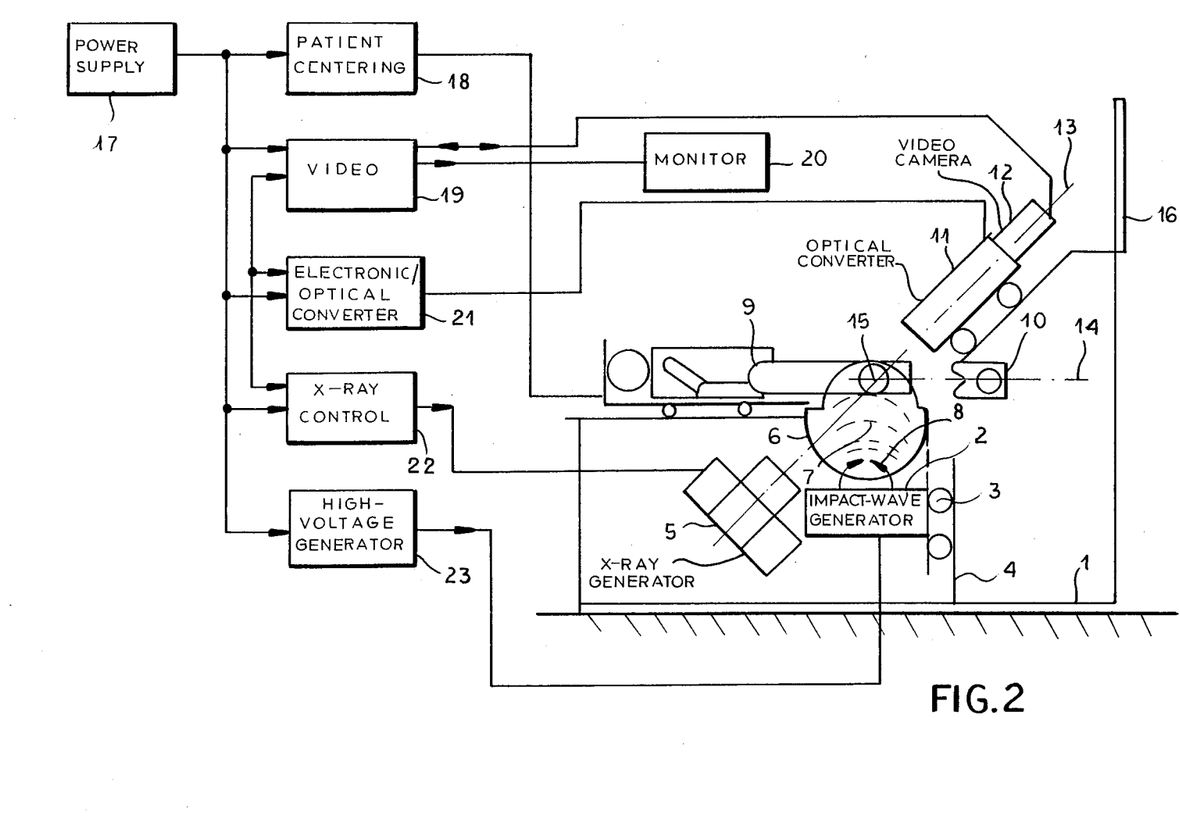
FIG. 2 is a general view of the apparatus with block circuit.

The apparatus for medical treatment of bone pathology comprises an outer housing 1, inside which there are disposed a generator of impact waves 2, on to the base of which there are fastened guiding rolls 3 which are in contact with the internal surface 4 of the outer housing 1, opposite to which there is disposed an x-ray generator 5. The top end of the generator of impact waves 2 is shaped as a vessel 6 which contains a transmitting medium, which is an acoustic liquid 7—water in this case, and it covers the high-voltage electrode 8 fastened to the bottom of the vessel 6, while in its top end there is disposed a flexible membrane 24. Over the generator of impact waves 2 there is disposed a patient carriage 9, opposite to which and over the generator of impact waves 2 there is disposed a light diaphragm 10, and over it there is disposed an electronic optical converter 11, to which there is connected a television camera 12. The longitudinal axis 13 of which coincides with the longitudinal axis of the x-ray generator 5, and its point of intersection with the longitudinal axis 14 of the light diaphragm 10 forms the point of action 15. To the outer housing 1, behind the television camera 12, there is positioned a protective barrier 16. The apparatus is connected to a block circuit which consists of a supply block 17, the output of which is connected to the block for centering the patient 18, and its output is connected to the carriage with the object 9. The output of the supply block 17 is also connected to the television block 19, while the latter, for its part, is connected to the monitor 20, the television camera 12 and the block of the electronic optical converter 21 which, for its part, is connected is connected via its output to the block of the x-ray system 22, which is connected to the input of the x-ray generator 5. The supply block 17 is directly connected to the block of the high-voltage generator 23 of the generator of impact waves 2, which are interconnected. The television block 19, the block of the electronic optical converter 21 and the x-ray block 22 are provided with feedforwards and feedbacks.

Figure 3:
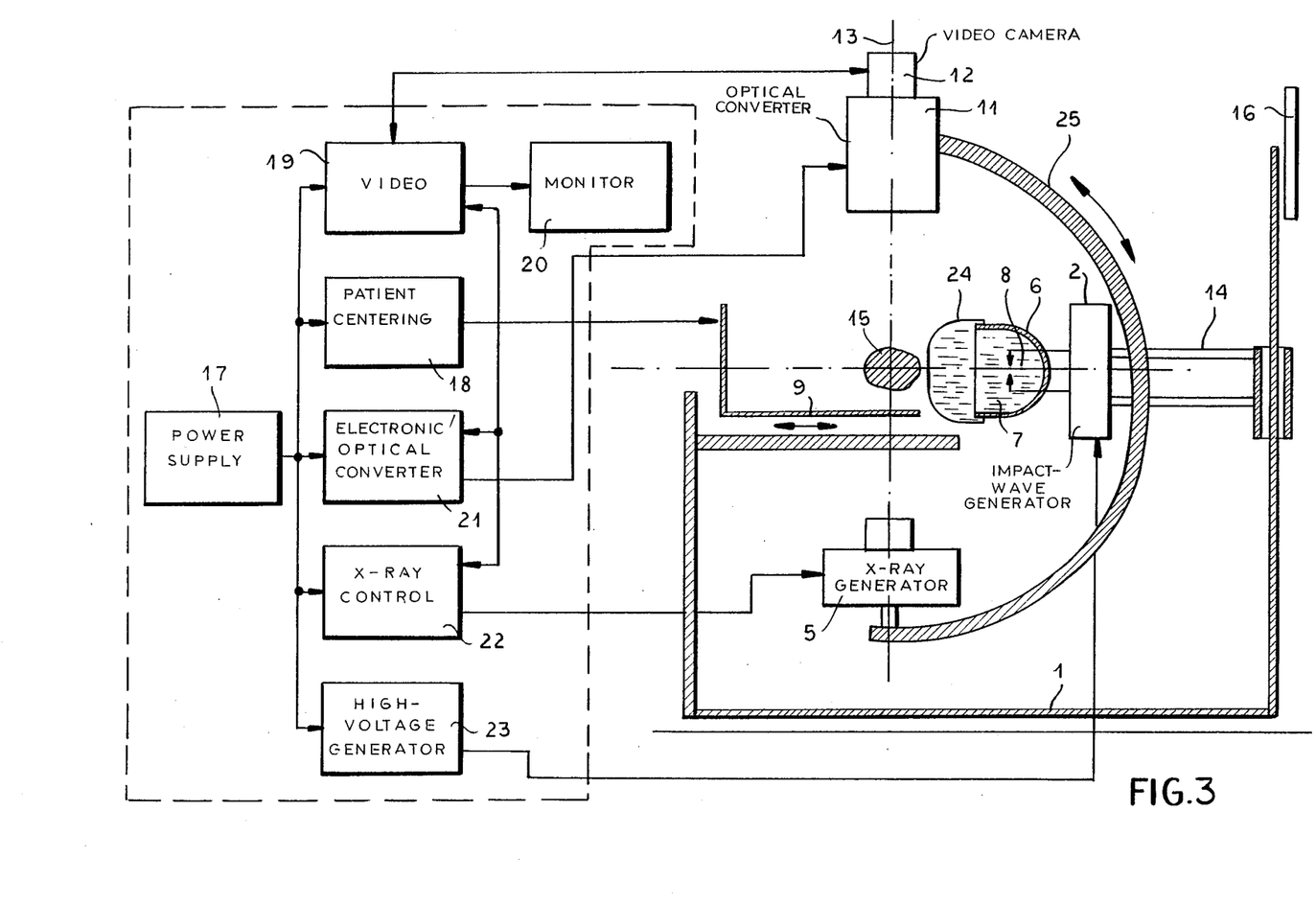
FIG. 3 is a general view of the apparatus with block circuit in a second modification.

The is also another preferred embodiment of the apparatus for medical treatment of bone pathology, which consists of an outer housing 1, to which there fastened movably to one of its ends a carrying arm, while to its other end there is attached a generator of electrohydraulic waves 2. Between the electrohydraulic generator 2 and the outer housing 1 there is fastened rigidly to the arm 14 an arch-shaped arm 25, to the bottom end of which there is fastened rigidly the x-ray generator 5, while to its top end there is fastened rigidly the electronic optical converter 11, to which the television camera 12 is fastened rigidly. The carrying arm 14 can rotate around its own axis at ±30°. To the generator of electrohydraulic waves 2 there is fastened rigidly a vessel for the transmitting medium 6, which contains an acoustic liquid 7—in this case water, and it covers the high-voltage electrode 8 which is fastened to the bottom of the vessel 6 for the transmitting medium, and to its top end there is fastened a flexible membrane 24. Opposite to the generator of electrohydraulic waves 2 there is disposed the carriage for centering the patient 9, on which the patient is lying with the point of action 15. To the outer housing 1 there is fastened rigidly a protective barrier 16.

The apparatus is connected to a block circuit, which consists of a supply block 17, the output of which is connected to the block for centering the patient 18, while its output is connected to the carriage with the object 9. The output of the supply block 17 is connected to the television block 19 which, for its part, is connected to the monitor 20, the television camera 12 and the block of the electronic optical converter 21, which is connected with its output to the block of the x-ray system 22, which is connected to the input of the x-ray generator 5. The supply block 17 is directly connected to the block of the high-voltage generator 23, which is connected to the generator of electrohydraulic waves 2. The television block 19, the electronic optical converter 21 and the x-ray system 22 are provided with feedforwards and feedbacks.

The invention is also explained by means of the following examples of medical treatment of bone pathology:

EXAMPLE 1

Figure 4:
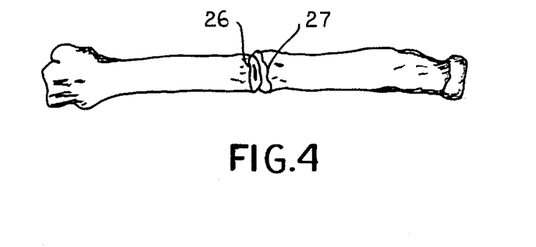
FIG. 4 is a general view of s radius bone with pseudoarthrosis.
Figure 5:
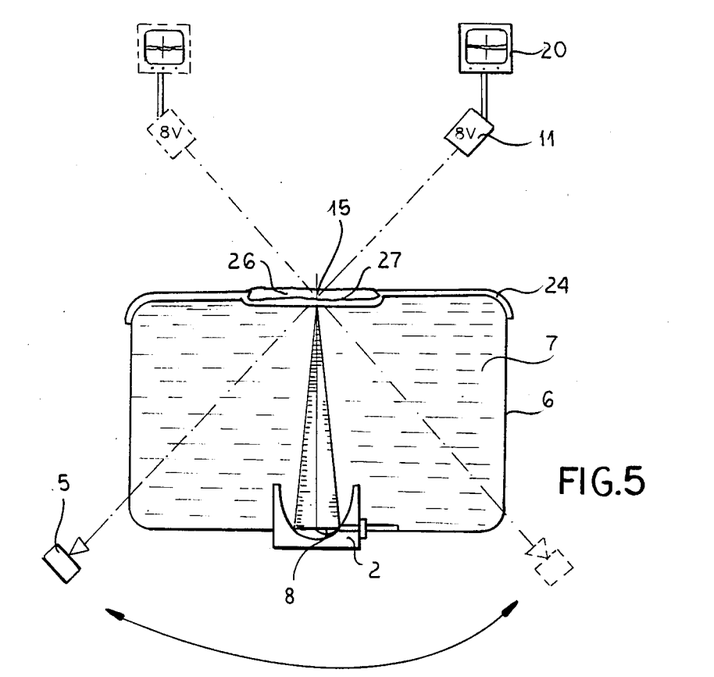
FIG. 5 shows how a radius bone with pseudoarthrosis is subjected to the action of impact waves.
Figure 6:
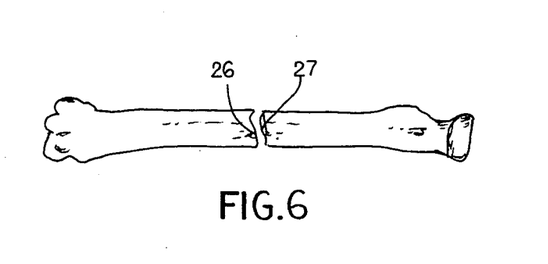
FIG. 6 is a general view of a radius bone with pseudoarthrosis after the action of impact waves.

FIG. 4 shows a pseudoarthrosis or delayed consolidation of a radius bone with a bottom edge 26 and an upper edge 27. A regional intravenous anesthesia of the limb with a non-healed radius bone is paerformed, and the latter is fixed to the patient carriage 9 shown in FIG. 1, being in contact with the flexible membrane 24 as shown in FIGS. 1 and 5. After the positioning of the point of action 15 there are delivered on the bone edge 26 1200 electrohydraulic impacts with a frequency of 2 impacts per second at a pressure of 1300 bars and a pulse duration of 3 microseconds over 20 minutes. The same actions are also applied to the upper bone edge 27. FIG. 6 shows the result of the action of the electrohydraulic impact waves with formation of bone sand admixed with blood coming from the opened microvessels and microfissures of the edges of the bone fragments 26 and 27. After the termination of the procedure the limb of the patient is released from the patient carriage 9 and there follows an external immobilization for 80 days.

EXAMPLE 2

Figure 7:
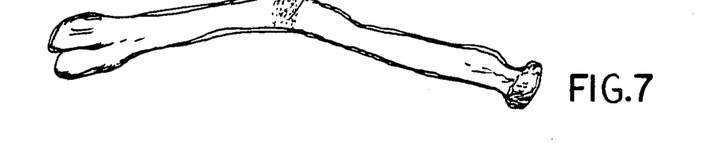
FIG. 7 is a general view of a deformed radius bone.
Figure 8:
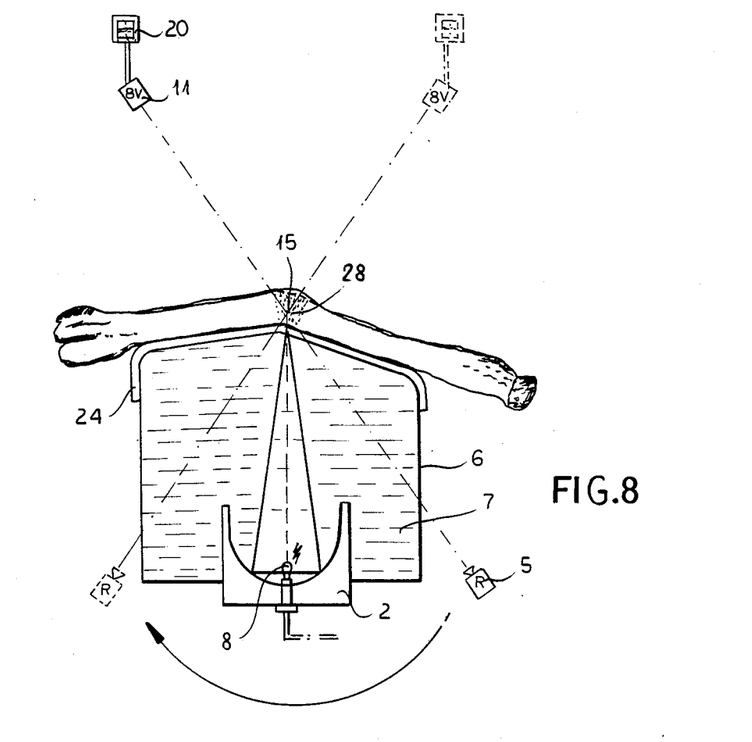
FIG. 8 shows how the deformed radius bone is subjected to the action of impact waves.
Figure 9:
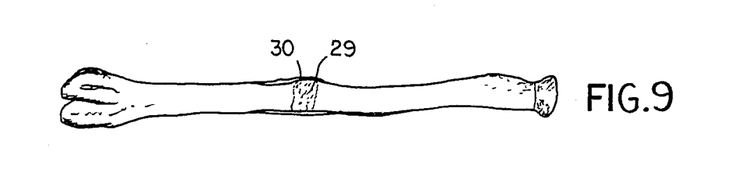
FIG. 9 is a general view of the deformed radius bone after the action and correction.
Figure 10:
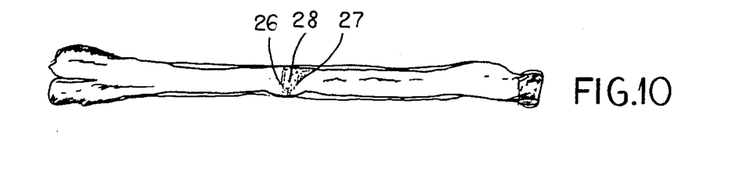
FIG. 10 is a general view of the bone after knit.

FIG. 7 shows the deformation of a radius bone 28. After performing a regional intravenous anesthesia of the limb with a deformed radius bone, the latter is fixed to the patient carriage 9 shown in FIG. 1, being in contact with the flexible membrane 24 as shown in FIGS. 1 and 8. After positioning, the point of action 15 is set up on the bone deformation 28. There are delivered 3000 electrohydraulic impacts with a frequency of 2 impacts per second at a pressure of 1500 bars and pulse duration of 3 microseconds over 50 minutes. FIG. 9 shows the result of the action of the electrohydraulic impact waves with formation of fracture of the deformation 29 at preserved periosteum 30 and subsequent manual correction of the deformation. After the termination of the procedure, there is carried out an external immobilization of the limb of the patient, which he must bear for 90 days. FIG. 10 shows the result with knit in straight position deformation of the radius bone 28.

EXAMPLE 3

Figure 11:
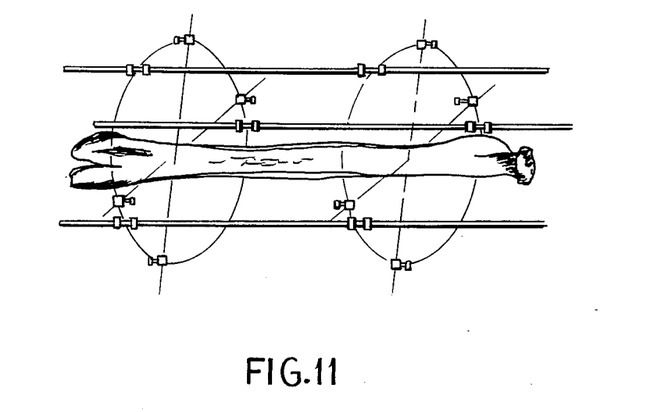
FIG. 11 shows a pathologically shortened radius bone placed in the apparatus for extrafocal fixation.
Figure 12:
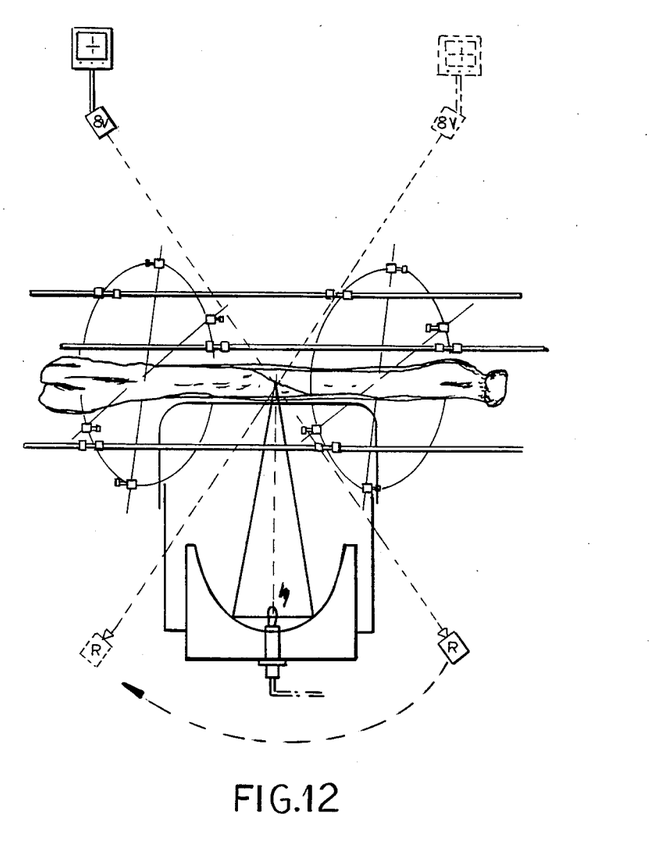
FIG. 12 shows the bone placed in the apparatus with diagrammatic illustration of the arrangement for action.
Figure 13:
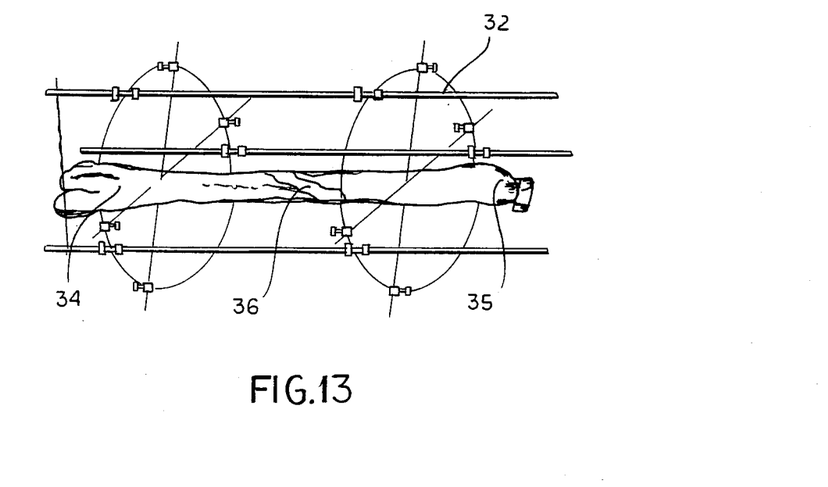
FIG. 13 shows the process of correction of the length of a radius bone according to FIG. 12.
Figure 14:
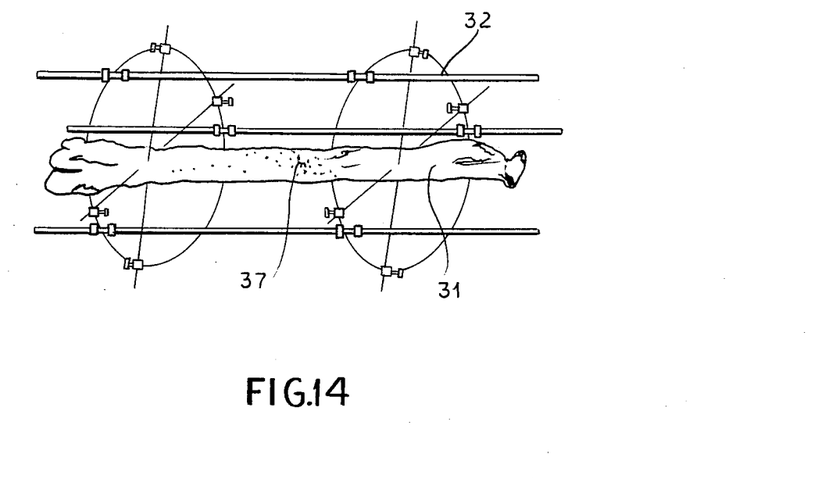
FIG. 14 shows the bone illustrated in FIG. 13—elongated and knit a normal state.

FIG. 11 shows a shortened tubular bone 31 mounted on an apparatus for extrafocal fixation 32, and before its mounting there is performed a regional intravenous anesthesia for upper limb or peridural anesthesia for bottom limb. The limb is fixed to the patient carriage 9 shown in FIG. 1 where it comes in contact with the flexible membrane 24 shown in FIG. 12. After positioning, the point of action 15 is set up on the tubular bone 31 subsequently in three spots, the distance between them being up to 20 mm, and in each spot there are delivered 1000 electrohydraulic impacts for the upper limb and 1900 electrohydraulic impacts for the bottom limb. FIG. 12 shows the result of the action in obtaining a fracture 33 of bone 31 at preserving the periosteum 30. FIG. 13 shows the elongation of the bone 31, consisting of two parts 34 and 35 after a fracture, which are extended by means of the apparatus 32 daily over 20 days until reaching the length of the sound limb. Between both parts 34 and 35 of the bone 31 there is obtained a gap 36, which is filled with blood and bone sand as a result of the action. After the elapsing of the 20 days, the apparatus with the elongated bone remains for immobilization until the total consolidation for 4 months; the healed and elongated zone of the bone 37 is shown in FIG. 14, the length of the bone 31 being normalized.

The apparatus for medical treatment of bone pathology according to the invention operates as follows:

After the switching-on of the supply block 17, a voltage is supplied to the block for centering the patient 18 and, as a result, the patient carriage with the object 9 is centered. Then the voltage is supplied to the x-ray block 22 which actuates the x-ray generator 5. The rays produced by the x-ray generator 5 are propagated along its longitudinal axis 13, they pass through the point of action 15 and reach the electronic optical converter 11, in the output of which there is obtained the image of action 15. The image is received by the television camera 12, the signal of which is transmitted to the television block 19, where it is processed and then transmitted to the monitor 20 and via the feedbacks to the block of the electronic optical converter 21 and the block of the television system 22. The voltage supplied by the supply block 17 passes through the block of the high-voltage generator 23 for the supply of the generator of impact waves 2. After entering a command in the block of the high-voltage generator 23 by electrode 8, the generator of impact waves 2 begins to generate impact waves, which via the acoustic medium 7 reach the point of action 15 of the object 9. This cycle is repeated until the necessary healing effect is achieved.

In a second modification of the apparatus, after switching-on the supply block 17, there is supplied a voltage to the block for centering the patient 18 and, as a result, the patient carriage with the object 9 is centered. Then a voltage is supplied to the x-ray system 22 which actuates the generator of x-rays 5. The rays produced by the x-ray generator 5 are propagated along its longitudinal axis 13. By rotation of the carrying arm 24 around its axis 14 there is achieved a rotation of the longitudinal axis 13 at ±30 degrees with respect to the axis 14, which is an axis of the generator of impact waves, thus achieving an accurate determination of the spot of action 15. Passing through the point of action 15, the rays reach the electronic optical converter 11, at the output of which there is obtained the image of the object of action 15. The image is received by the television camera 12, the signal of which is transmitted to the television block 19, where it is processed and transmitted to the monitor 20 and via the feedbacks—to the block of the electronic optical converter 21 and the block of the x-ray system 22. The voltage supplied by the supply block 17 passes through the block of the high-voltage generator 23 for supplying the generator of impact waves 2. After entering a command in the block of the high-voltage generator 23 by electrode 8, the generator of impact waves 2 begins to generate impact waves, which via the acoustic medium 7 reach the point of action 15 of the object 9. This cycle is repeated until the necessary healing effect is achieved.

The impact waves can also be produced by an ultrasonic generator of impact waves, a magnetostriction generator of impact waves or a microexplosive generator of impact waves.

The scope of the invention is not limited only to the aforementioned generator types. It should be understood that there can also be used other generators which can generate impact waves and can be used for medical treatment of bone pathology.

CITED LITERATURE

1. Diffenbach-Beck. Cited in I. Koptchev, "Trawmatologya na oporno-dvigatelnya aparat", Sofia, Medizina i Fizkoultoura, 1976, p. 137.

We claim:

1. A method of medically treating a patient suffering from a pathological bone condition of a limb, which comprises the steps of:
   (a) anesthetizing the patient;
   (b) fixing the limb affected with the pathological bone condition and centering its pathological site;
   (c) treating the pathological site, once, consecutively, and extracorporeally with impact waves of from 300 to 6000 impacts with a frequency of impacts of from 0.5 to 4 per second at a pressure of from 700 to 2500 bars and a pulse duration of from 0.5 to 4 microseconds for a period of 10 to 120 minutes; and
   (d) subsequently immobilizing the limb for a period of from 15 to 90 days.

2. Method for medical treatment of bone pathology according to claim 1, wherein the treatment of the pathological site is effected by impact waves of from 1000 to 5000 impacts with a frequency of from 1 to 2 per second at a pressure of from 1200 to 2000 bars, and pulse duration of from 1.5 to 3 microseconds over 20 to 110 minutes, with a subsequent immobilization for a period of from 40 to 90 days.

3. Method for medical treatment of bone pathology according to to claim 2, wherein the impact waves acting on the pathological site are electrohydraulic.

4. Method for the medical treatment of bone pathology according to claim 1, wherein the bone is fixed with an extrafocal fixator and the pathological site is subjected to the action of impact waves of from 1000 to 6000 impacts with a frequency of from 1 to 3 per second at a pressure of from 1100 to 1700 bars and pulse duration of from 1 to 3.5 microseconds over 30 to 115 minutes with a subsequent immobilization for a period of from 60 to 85 days.

5. Method for medical treatment of bone pathology according to claim 1, wherein the pathological site is subjected to the action of impact waves of from 750 to 6000 impacts with a frequency of from 0.5 to 3.5 per second at a pressure of from 1200 to 2500 bars and pulse duration of from 0.5 to 2.5 microseconds over 15 to 120 minutes with a subsequent immobilization for a period of from 30 to to 80 days.

6. Method for medical treatment of bone pathology according to claim 1, wherein the pathological site is subjected to the action of impact waves of from 300 to 3000 impacts with a frequency of from 1 to 3.5 per second at a pressure of from 700 to 1500 bars and pulse duration of from 1.5 to 4 microseconds during 10 to 90 minutes, with a subsequent immobilization for a period of from 15 to 60 days.

7. Method for medical treatment of bone pathology according to claim 1, wherein the pathological site is subjected to the action of impact waves of from 500 to 5000 impacts with a frequency of from 0.5 to 4 per second, at a pressure of from 850 to 1700 bars and pulse duration of from 1.5 to 3.5 microseconds over 15 to 95 minutes, with a subsequent immobilization on for a period of from 15 to 60 days.

8. Method for medical treatment of bone pathology according to claim 1, wherein the pathological site is subjected to the action of impact waves of from 1000 to 5500 impacts with a frequency of from 1 to 4 per second, at a pressure of from 950 to 1900 bars and pulse duration of from 0.5 to 3.5 microseconds over 20 to 110 minutes, with a subsequent immobilization for a period of from 15 to 90 days.

9. Method for medical treatment of bone pathology according to claim 1, wherein the pathological site is subjected to the action of impact waves of from 350 to 4000 impacts with a frequency of from 1 to 2.5 per second at a pressure of from 150 to 1600 bars and pulse duration of from 1.5 to 3 microseconds over 10 to 105 minutes, with a subsequent immobilization for a period of from 15 to 30 days.

* * * * *